United States Patent
Jo et al.

(10) Patent No.: US 8,758,226 B2
(45) Date of Patent: Jun. 24, 2014

(54) IMAGE SENSOR FOR CAPSULE TYPE ENDOSCOPE HAVING FRAME PUNCTURING FUNCTION AND METHOD FOR PROCESSING IMAGE DATA THEREOF

(75) Inventors: Wan-Hee Jo, Chungcheongbuk-do (KR); Jang-Sik Moon, Chungcheongbuk-do (KR)

(73) Assignee: Intellectual Ventures II LLC, Wilmington, DE (US)

( * ) Notice: Subject to any disclaimer, the term of this patent is extended or adjusted under 35 U.S.C. 154(b) by 2533 days.

(21) Appl. No.: 11/453,985

(22) Filed: Jun. 16, 2006

(65) Prior Publication Data
US 2006/0287573 A1    Dec. 21, 2006

(30) Foreign Application Priority Data

Jun. 17, 2005   (KR) .................. 10-2005-0052336
May 17, 2006   (KR) .................. 10-2006-0044165

(51) Int. Cl.
   *A61B 1/04*   (2006.01)
   *A62B 1/04*   (2006.01)
(52) U.S. Cl.
   USPC .............. 600/109; 600/117; 600/118; 348/65
(58) Field of Classification Search
   USPC ............ 600/101, 109, 117, 118, 424; 348/65, 348/74
   See application file for complete search history.

(56) References Cited

U.S. PATENT DOCUMENTS

| | | | | |
|---|---|---|---|---|
| 6,428,469 | B1* | 8/2002 | Iddan et al. | 600/109 |
| 7,104,952 | B2* | 9/2006 | Iddan et al. | 600/118 |
| 7,144,366 | B2* | 12/2006 | Takizawa et al. | 600/117 |
| 2004/0165104 | A1* | 8/2004 | Takami | 348/372 |
| 2004/0193010 | A1* | 9/2004 | Fujimori et al. | 600/118 |
| 2005/0047279 | A1* | 3/2005 | Ito | 368/10 |
| 2005/0054897 | A1* | 3/2005 | Hashimoto et al. | 600/118 |
| 2005/0183733 | A1* | 8/2005 | Kawano et al. | 128/899 |
| 2005/0215911 | A1* | 9/2005 | Alfano et al. | 600/476 |
| 2006/0058652 | A1* | 3/2006 | Little | 600/437 |
| 2006/0155174 | A1* | 7/2006 | Glukhovsky et al. | 600/301 |

FOREIGN PATENT DOCUMENTS

| | | |
|---|---|---|
| JP | 2001-224553 | 8/2001 |
| KR | 2003-0039221 | 5/2003 |
| KR | 2004-44232 | 5/2004 |

* cited by examiner

*Primary Examiner* — Philip R Smith
*Assistant Examiner* — Rynae Boler
(74) *Attorney, Agent, or Firm* — McAndrews, Held & Malloy, Ltd.

(57) ABSTRACT

An image sensor for a capsule type endoscope in which an image data is processed in frame units, the image sensor having analog and digital circuits, the image sensor includes a frame-puncturing unit for interrupting a power supply to the analog circuit at a predetermined frame among a plurality of frames. The image sensor may include a start delay unit for delaying a power supply to the analog circuit for a desired time.

21 Claims, 2 Drawing Sheets

1st VSYNC START POINT

| ANALOG | ANALOG | /////// | ANALOG | /////// | ANALOG | /////// | ANALOG | /////// |
| DIGITAL | DIGITAL | /DIGITAL/ | DIGITAL | /DIGITAL/ | DIGITAL | /DIGITAL/ | DIGITAL | /DIGITAL/ |

1st VSYNC START POINT

| ANALOG | ANALOG | /////// | /////// | /////// | ANALOG | /////// | /////// | /////// |
| DIGITAL | DIGITAL | /DIGITAL/ | /DIGITAL/ | /DIGITAL/ | DIGITAL | /DIGITAL/ | /DIGITAL/ | /DIGITAL/ |

1st VSYNC START POINT

IMAGE SENSOR FOR CAPSULE TYPE ENDOSCOPE HAVING FRAME PUNCTURING FUNCTION AND METHOD FOR PROCESSING IMAGE DATA THEREOF

FIELD OF THE INVENTION

The present invention relates to an image sensor; and, more particularly, to an image sensor for a capsule type endoscope used in technology of capturing images inside a human body, and a method for processing image data thereof.

DESCRIPTION OF RELATED ART

An endoscope, which is a representative one among a variety of apparatuses for capturing images for body's internal structure, is used for providing upper and lower images of a stomach or intestines and thus, it is widely used in a field of medicine.

A capsule type endoscope is a capsule type subminiature endoscope enabling a doctor to directly examine the intestines or an internal structure of a coelom through a video screen or a computer monitor, when a patient swallows the capsule endoscope like a pill.

Many patients prefer taking medication to the endoscopic examination because the traditional endoscope brings about pain, indisposition, etc. during the examination. Therefore, in order to overcome the above disadvantages of the typical endoscope, a capsule endoscope has been introduced. In particular, the capsule type endoscope has been developed in order that it may be used for diagnosing disease in the small intestine which is the longest internal organ among gastrointestinal systems.

Meanwhile, since the capsule type endoscope takes images repeatedly in a state that an external power supply is interrupted while staying in a human body for a long time, an extremely low power capsule type endoscope is increasingly demanded.

FIG. 1 is a table setting forth power supply/interruption states of analog and digital circuits for each image data frame in a typical image sensor for a capsule type endoscope.

The image data is processed in the capsule type endoscope such that the power is supplied to the analog and digital circuits for every image data frame.

However, when the capsule type endoscope passes slowly through the gastrointestinal tract, there is unnecessary power consumption because the power is still supplied to the analog and digital circuits for every image data frame. In more detail, the capsule type endoscope may move slowly in a specific internal organ such as an esophagus or the like due to the vermiculation so that captured images for one portion of the internal organ are transferred to an exterior as plenty of image data frames. In addition, until the capsule type endoscope finds out the diseased part, it captures and transmits unnecessary image data frames, which causes the power to be unnecessarily consumed after all.

This unnecessary power consumption is a very important limitation because the capsule type endoscope merely receives the power required for operating the system for several hours that it passes through the gastrointestinal tract only from its own power source.

Moreover, if a target internal organ that the capsule type endoscope will capture images is far from the mouth, the unnecessary power consumption is severe because the capsule type endoscope captures unnecessary images while moving to the target internal organ.

SUMMARY OF THE INVENTION

It is, therefore, an object of the present invention to provide an image sensor for a capsule type endoscope having a frame-puncturing function for extremely low power consumption, and a method for processing image data thereof.

It is another object of the present invention to provide an image sensor for a capsule type endoscope having a frame-puncturing function for generating predetermined frames among a plurality of successive frames in a state that a power supply to an analog circuit is selectively interrupted, and a method for processing image data thereof.

It is still another object of the present invention to provide an image sensor for a capsule type endoscope having a frame-puncturing function for interrupting a power supply to an analog circuit till the capsule type endoscope arrives at a target internal organ, and a method for processing image data thereof.

In accordance with an aspect of the present invention, there is provided an image sensor for a capsule type endoscope in which image data is processed in frame units, the image sensor including an analog circuit and a digital circuit, the image sensor including: a frame-puncturing unit for interrupting a power supply to the analog circuit at a predetermined frame among a plurality of frames.

In accordance with another aspect of the present invention, there is provided an image sensor for a capsule type endoscope in which image data is processed in frame units, the image sensor including an analog circuit and a digital circuit, the image sensor including: a start delay unit for delaying a power supply to the analog circuit for a desired time.

In accordance with still another aspect of the present invention, there is provided a method for processing image data of an image sensor for a capsule type endoscope, in which image data is processed in frame units, the image sensor including an analog circuit and a digital circuit, the method including: interrupting a power supply to the analog circuit till the capsule type endoscope arrives at a target internal organ; and supplying a power to the analog circuit when the capsule type endoscope arrives at the target internal organ.

BRIEF DESCRIPTION OF THE DRAWINGS

The above and other objects and features of the present invention will become better understood with respect to the following description of the preferred embodiments given in conjunction with the accompanying drawings, in which.

DETAILED DESCRIPTION OF THE INVENTION

An image sensor for a capsule type endoscope having a frame puncturing function and a method for processing an image data thereof in accordance with exemplary embodiments of the present invention will be described in detail with reference to the accompanying drawings.

Figure 1:
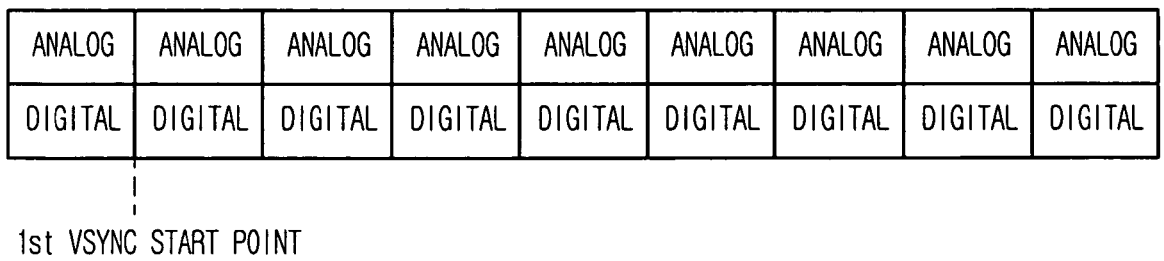
FIG. 1 is a table setting forth power supply/interruption states of analog and digital circuits for each image data frame in a typical image sensor for a capsule type endoscope.
Figure 2:
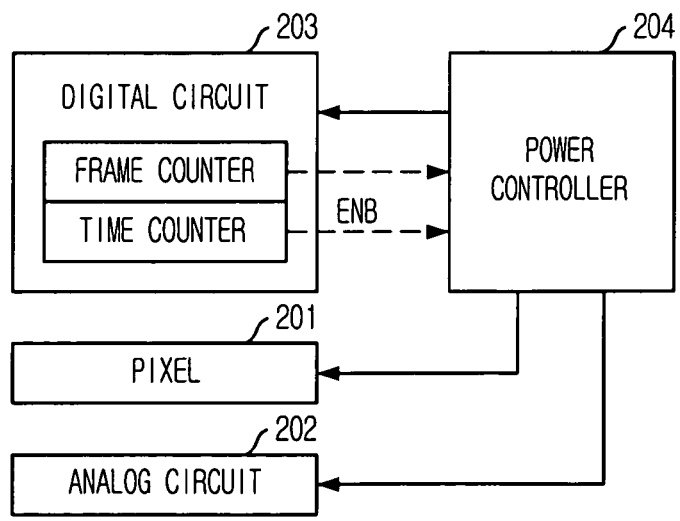
FIG. 2 is a block diagram setting forth an image sensor for a capsule type endoscope in accordance with an embodiment of the present invention.

FIG. 2 is a block diagram setting forth an image sensor for a capsule type endoscope in accordance with an embodiment of the present invention.

The image sensor for the capsule type endoscope in which an image data is processed in frame units, includes a pixel 201, an analog circuit 202, a digital circuit 203 and a power controller 204. The pixel 201 converts an optically captured image into an electrical analog image signal. The analog circuit 202 removes a noise such as a fixed pattern noise (FPN) by filtering the analog image signal and then, adjusts the analog image signal into a predetermined level so as to output a digital image signal. The digital circuit 203 processes the digital image signal and generates an operation signal of the analog circuit 202. The power controller 204 supplies a power to the pixel 201, the analog circuit 202, and the digital circuit 203 in response to a predetermined control signal of the digital circuit 203.

The digital circuit 203 is configured with a frame counter for counting an individual frame, and a time counter for counting a time. In more detail, the frame counter, which is included in a frame-puncturing unit for interrupting the power supply to the analog circuit 202 at a predetermined frame among a plurality of frames, selects the predetermined frame. If the value of the frame counter reaches a target value, it controls the power controller 204 to interrupt the power supply to the analog circuit 202. It is possible to interrupt the power supply to the digital circuit 203 except the frame counter and the time counter as well as the power supply to the analog circuit 202. Afterwards, the power is supplied again to the analog circuit 202 and the digital circuit 203 so as to generate some frames, and subsequently, the power supply to the analog and digital circuits 202 and 203 are interrupted again. Such a series of operations that the power is supplied/interrupted are repeated.

When a power is supplied again at a desired frame to the analog circuit 202 (including the digital circuit 203 except the frame counter and the time counter) in which the power supply has been interrupted, it needs a settling time.

The time counter, which is included in a start delay unit for delaying the power supply to the analog circuit 202 for a desired time after the first power supply, counts the desired time, i.e., a required time that the capsule type endoscope arrives at the target internal organ. Like the frame counter, it is possible to interrupt the power supply to the digital circuit 203 except the time counter and the frame counter. In this manner, the power supply/interruption of the analog and digital circuits are repeated.

A power control signal ENB will be explained in more detail in FIG. 4.

Figures 3A, 3B, 4:
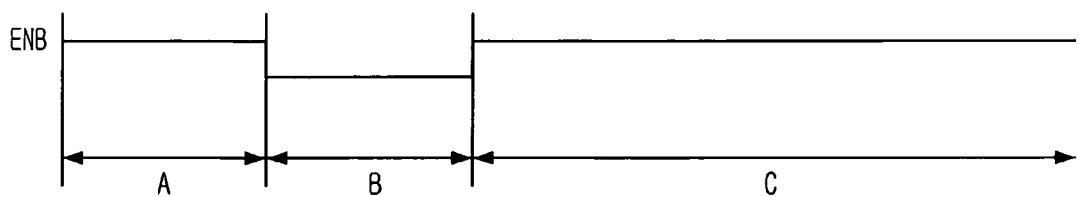
FIGS. 3A and 3B are tables setting forth power supply/interruption states of analog and digital circuits for each image data frame in the image sensor for the capsule type endoscope of FIG. 2.
FIG. 4 is a timing diagram setting forth activation/deactivation states of a power control signal which is responsive to a time counter of FIG. 2.

FIGS. 3A and 3B are tables setting forth supply/interruption states of analog and digital circuits for each image data frame in the image sensor for the capsule type endoscope of FIG. 2.

Referring to FIGS. 3A and 3B, the power supply to the analog circuit 202 is selectively interrupted at predetermined image data frame units in order to reduce the unnecessary power consumption. That is, the image data frame transferred to an image output unit, e.g., a monitor, is divided into an effective image data frame and a punctured frame. Herein, the effective image data frame means a normal frame generated when the digital circuit and the analog circuit are normally operate, whereas the punctured frame means a frame generated when the power is not supplied to the analog circuit (including the digital circuit except the apparatus concerned with the power supply, e.g., the frame counter).

Hereinafter, an operational mode when the effective image data frame is generated is referred to as a normal operational mode, and an operational mode when the punctured framed is generated is referred to as a selective operational mode.

FIG. 3A indicates an operation of the image sensor for the capsule type endoscope in which the normal operational mode and the selective operational mode are performed in a ratio of approximately 1 to approximately 1. FIG. 3B illustrates an operation of the image sensor for the capsule type endoscope in which the normal operational mode and the selective operational mode are performed in a ratio of approximately 1 to approximately 3. The frames are discarded till a vertical synchronous signal VSYNC is come out, wherein the vertical synchronous signal VSYNC is controlled at the digital circuit 203 (see FIG. 2).

In more detail, when a test period for confirming whether or not the capsule type endoscope operates normally is finished and the vertical synchronous signal VSYNC is activated, a first effective image data frame is generated and the frame counter is initialized. The value of the selective operation mode is set to be approximately 0.5 as a set value.

Subsequently, the initialized frame counter and the set value of the selective operational mode are compared with each other. Since the value of the frame counter is approximately 0 and the set value of the selective operational mode is approximately 0.5, the power supply to the analog circuit 202 (see FIG. 2) is interrupted.

Thereafter, if the value of the frame counter increases to be approximately 1 which is greater than the set value of the selective operational mode, i.e., approximately 0.5, the power is supplied to the analog circuit 202 (see FIG. 2) to generate an effective image data frame.

In FIG. 3A, the set value of the selective operational mode is set to be approximately 0.5 for making the ratio between the normal operation mode and the selective operational mode be approximately 1 to approximately 1. Meanwhile, if making the set value of the selective operational mode be approximately 2.5, the ratio between the normal operational mode and the selective operational mode may be 1:3 as illustrated in FIG. 3B.

The time counter is an apparatus for transmitting the power control signal ENB to the power controller 204 to interrupt the power supply to the analog circuit 202, which will be more fully illustrated herebelow.

FIG. 4 is a timing diagram setting forth activation/deactivation states of a power control signal which is responsive to the time counter of FIG. 2.

The power control signal ENB is responsive to the time counter of the image sensor for the capsule type endoscope, and it is a signal required for observing the diseased part of the stomach or the intestines which is far from the mouth. As aforementioned already, once the capsule type endoscope including the image sensor is injected inside the human body through the mouth, there is unnecessary power consumption because unnecessary image data frames are transferred till the capsule type endoscope arrives at the target internal organ. However, in order to reduce the unnecessary power consumption, there exist three periods in the inventive image sensor for the capsule type endoscope, i.e., a test period A, a standstill period B, and a normal operation period C according to the activation/deactivation state of the power control signal ENB, as depicted in FIG. 4.

The test period A is a period to test whether or not the capsule type endoscope normally operates in the internal organs when the power is supplied first after it is injected through the mouth. The standstill period B is a period to interrupt the power supply to the analog circuit 202 (see FIG. 2) till the capsule type endoscope arrives at the target internal organ. The normal operation period C is a period to capture the images of the diseased part after the capsule type endoscope has arrived at the target internal organ. The power control signal ENB is activated in both the test period A and the normal operation period C, but it is deactivated in the standstill period B.

In addition, it is possible to interrupt the power supply to the digital circuit 203 (see FIG. 2) except the apparatus concerned with the power supply, e.g., the time counter of the digital circuit 203 (see FIG. 2), as well as the power supply to the analog circuit 202 (see FIG. 2). Before the captured images are transferred again after the standstill period B, the setting time is needed to receive the image.

During the normal operation period C, the punctured frame is generated using the frame counter so that it is possible to effectively save the power even during the normal operation period C. The apparatus and method for generating the punctured frame have been already illustrated and thus, descriptions for them will be omitted herein.

As described above, the inventive image sensor for the capsule type endoscope saves power by interrupting the power supply to the analog circuit (including the digital circuit except the frame counter) at a predetermined frame among a plurality of successive frames. In addition, after supplying the power first, the power supply to the analog circuit (including the digital circuit except the frame counter) is interrupted for a desired time and thus it is also possible to save power.

As illustrated above, the power can be selectively supplied to the analog circuit (including the digital circuit except the frame counter and the time counter) or can be interrupted to reduce unnecessary power consumption so that the power is effectively used.

In addition, the power supply to the analog circuit is interrupted till the capsule type endoscope arrives at the target internal organ.

In conclusion, according to this embodiment of the present invention, it is possible to obtain the image sensor which acts more effectively, and the capsule type endoscope having the image sensor, because the unnecessary; power consumption can be reduced effectively.

Meanwhile, there is a limitation in the size of the capsule type endoscope because the capsule type endoscope is an apparatus which moves inside the human body. However, according to this embodiment of the inventive image sensor for the capsule type endoscope, the size of the power source determining the total size of the capsule type endoscope can be reduced so that it is possible to capture the images for body's internal structure effectively and stably.

The present application contains subject matter related to the Korean patent application Nos. KR 2005-0052336 and 2006-0044165 respectively filed in the Korean Patent Office on Jun. 17, 2005 and May 17, 2006, the entire contents of which being incorporated herein by reference.

While the present invention has been described with respect to certain preferred embodiments, it will be apparent to those skilled in the art that various changes and modifications may be made without departing from the spirit and scope of the invention as defined in the following claims.

What is claimed is:

1. A method for processing image data of an image sensor for a capsule-type endoscope, the method comprising: interrupting power being supplied to an analog circuit of the image sensor until the capsule-type endoscope arrives at a target internal organ; and
supplying power to the analog circuit when the capsule-type endoscope arrives at the target internal organ;
wherein the image data is processed in frames; and
wherein said supplying power to the analog circuit comprises interrupting the power being supplied to the analog circuit at a predetermined frame among a plurality of frames.

2. The method of claim 1, before said interrupting power being supplied to an analog circuit, further comprising supplying power for testing the capsule-type endoscope.

3. A method for processing image data of a capsule-type endoscope, the method comprising:
powering an analog circuit of the capsule-type endoscope that is configured to process analog image signals;
powering a first portion of a digital circuit of the capsule-type endoscope; and
interrupting power to the analog circuit in response to the first portion indicating that power to the analog circuit is to be interrupted;
wherein said powering an analog circuit comprises powering the analog circuit during a test period following ingestion of the capsule-type endoscope; and
wherein said interrupting power comprises interrupting power to the analog circuit in response to completion of the test period.

4. The method of claim 3, wherein:
the first portion comprises a time counter; and
said interrupting power comprises interrupting power to the analog circuit until the time counter has a predetermined count associated with an expected time for the capsule-type endoscope to arrive at a target internal organ.

5. The method of claim 3, further comprising interrupting power to a second portion of the digital circuit in response to completion of the test period.

6. A method for processing image data of a capsule-type endoscope, the method comprising:
powering an analog circuit of the capsule-type endoscope that is configured to process analog image signals;
powering a first portion of a digital circuit of the capsule-type endoscope; and
interrupting power to the analog circuit in response to the first portion indicating that power to the analog circuit is to be interrupted;
wherein the first portion comprises a frame counter; and
wherein said interrupting power comprises interrupting power to the analog circuit in response to the frame counter indicating the analog circuit has processed a first predetermined number of frames from the analog image signal.

7. The method of claim 6, further comprising restoring power to the analog circuit in response to the frame counter indicating a second predetermined number of frames from the analog image signal have passed since interrupting power to the analog circuit.

8. The method of claim 6, further comprising interrupting power to a second portion of the digital circuit in response to the frame counter indicating the analog circuit has processed the first predetermined number of frames of the analog image signal.

9. The method of claim 6, further comprising restoring power to the analog circuit and the second portion of the digital circuit in response to the frame counter indicating a second predetermined number of frames from the analog image signal have passed since interrupting power to the analog circuit.

10. The method of claim 6, further comprising:
powering a pixel configured to generate the analog image signal; and
interrupting power to the pixel in response to the first portion indicating that power to the analog circuit is to be interrupted.

11. The method of claim 6, further comprising:
receiving status signals from the first portion; and
determining, based on the status signals, whether power to the analog circuit is to be interrupted.

12. A method of operating a capsule-type endoscope, the method comprising:
generating an analog image signal in response to powering a pixel of the capsule-type endoscope;
processing the analog image signal in response to powering an analog circuit of the capsule-type endoscope;
interrupting power to the analog circuit in response to determining that power to the analog circuit is to be interrupted;
powering the analog circuit during a test period following ingestion of the capsule-type endoscope; and
determining that power to the analog circuit is to be interrupted in response to completion of the test period.

13. The method of claim 12, further comprising interrupting power to the pixel in response to determining that power to the analog circuit is to be interrupted.

14. The method of claim 12, further comprising:
interrupting power to the analog circuit after ingestion of the capsule-type endoscope;
updating a timer counter of the capsule-type endoscope after said interrupting power to the analog circuit; and
restoring power to the analog circuit in response to the time counter indicating an expected time for the capsule-type endoscope to arrive at a target internal organ has elapsed.

15. A method of operating a capsule-type endoscope, the method comprising:
generating an analog image signal in response to powering a pixel of the capsule-type endoscope;
processing the analog image signal in response to powering an analog circuit of the capsule-type endoscope;
interrupting power to the analog circuit in response to determining that power to the analog circuit is to be interrupted;
updating a frame counter of the capsule-type endoscope in response to processing frames of the analog image signal; and
determining that power to the analog circuit is to be interrupted in response to the frame counter indicating a first predetermined number of frames have been processed.

16. The method of claim 15, further comprising restoring power to the analog circuit in response to the frame counter indicating a second predetermined number of frames have passed since interrupting power to the analog circuit.

17. The method of claim 15, further comprising interrupting power to the pixel in response to the frame counter indicating the first predetermined number of frames have been processed.

18. The method of claim 17, further comprising restoring power to the analog circuit and the pixel in response to the frame counter indicating a second predetermined number of frames have passed since interrupting power to the analog circuit.

19. The method of claim 3, further comprising:
powering a pixel configured to generate the analog image signal; and
interrupting power to the pixel in response to the first portion indicating that power to the analog circuit is to be interrupted.

20. The method of claim 3, further comprising:
receiving status signals from the first portion; and
determining, based on the status signals, whether power to the analog circuit is to be interrupted.

21. The method of claim 15, further comprising interrupting power to the pixel in response to determining that power to the analog circuit is to be interrupted.

* * * * *